United States Patent

Carle et al.

[11] Patent Number: 5,167,790
[45] Date of Patent: Dec. 1, 1992

[54] FIELD-INVERSION GEL ELECTROPHORESIS

[75] Inventors: Georges F. Carle; Maynard V. Olson, both of St. Louis, Mo.

[73] Assignee: Washington University, St. Louis, Mo.

[21] Appl. No.: 526,772

[22] Filed: May 18, 1990

Related U.S. Application Data

[63] Continuation of Ser. No. 178,676, Apr. 7, 1988, abandoned, which is a continuation-in-part of Ser. No. 781,283, Sep. 27, 1985, Pat. No. 4,737,251.

[51] Int. Cl.$^5$ .................. G01N 27/26; B01D 57/02
[52] U.S. Cl. .................. 204/299 R; 204/182.8
[58] Field of Search ............ 204/299 R, 182.8, 180.1, 204/182.9, 182.7

[56] References Cited

U.S. PATENT DOCUMENTS

| | | | |
|---|---|---|---|
| Re. 27,245 | 12/1971 | Buerkel | 361/245 X |
| 2,442,585 | 6/1948 | Campbell et al. | 363/63 |
| 2,935,454 | 5/1960 | Tokumoto | 204/DIG. 9 X |
| 3,423,306 | 1/1969 | Hurwitz | 204/299 R |
| 3,470,080 | 9/1969 | Raymond et al. | 204/182.8 |
| 3,471,768 | 10/1969 | Doyle et al. | 363/63 |
| 3,506,554 | 4/1970 | Broome | 204/180.1 |
| 3,515,664 | 6/1970 | Johnson et al. | 204/301 |
| 3,522,518 | 8/1970 | Dybvig et al. | 363/63 |
| 3,567,611 | 3/1971 | Birmingham et al. | 204/182.8 |
| 3,630,882 | 12/1971 | Dilworth, III | 204/200 R |
| 3,694,335 | 9/1972 | Pretorius et al. | 204/180.1 |
| 3,712,859 | 1/1973 | Dilworth, III | 204/182.8 |
| 3,720,593 | 3/1973 | Juhos | 204/182.8 |
| 3,766,048 | 10/1973 | Flygare et al. | 204/299 R |
| 4,148,703 | 4/1979 | Trop et al. | 204/182.1 |
| 4,224,529 | 9/1980 | Fujiwara | 361/246 X |
| 4,312,727 | 1/1982 | Shainoff | 204/182.8 |
| 4,430,178 | 2/1984 | Anderson et al. | 204/DIG. 9 X |
| 4,473,452 | 9/1984 | Cantor et al. | 204/182.8 |
| 4,517,059 | 5/1985 | Loch et al. | 204/DIG. 9 X |
| 4,597,837 | 7/1986 | Oda et al. | 204/28 X |
| 4,737,251 | 4/1988 | Carle et al. | 204/182.8 |

FOREIGN PATENT DOCUMENTS 1046370 12/1958 Fed. Rep. of Germany.

OTHER PUBLICATIONS

Gilles Roy et al. "Inexpensive and simple set-up for field inversion gel electrophoresis" Nucleic Acids Research, vol. 16, No. 2, (Jan. 25, 1988) p. 768.
T. H. N. Ellis et al "Ramped field inversion gel electrophoresis: a cautionary note" Nucleic Acid Research, vol. 15, No. 13 (Jul. 10, 1987) p. 5489.
Hugh J. S. Dawkins et al "Field inversion gel electrophoresis (FIGE) in vertical slabs as an improved method for large DNA separation" Nucleic Acids Research, vol. 15, No. 8 (Apr. 24, 1987), pp. 3634-3635.
Georges F. Carle et al "Electrophoretic Separations of Large DNA Molecules by Periodic Inversion of the Electric Field" Science vol. 232 (Apr. 4, 1986) 65-68.
Rickwood et al., Gel Electrophoresis of Nucleic Acids: A Practical Approach, IRL Press, Oxford, United Kingdom, pp. 110-117.
Fangman, *Nucleic Acids Res.* 5:653-665 (1978).
Serwer, *Biochem.* 19:3001-3004 (1980).
Schwartz et al., "Cold Spring Harbor Sym. Quant. Biol." 47:189-195 (1983).
Schwartz et al., *Cell* 37:67-75 (1984).

(List continued on next page.)

Primary Examiner—John Niebling
Assistant Examiner—John S. Starsiak, Jr.
Attorney, Agent, or Firm—Morrison & Foerster

[57] ABSTRACT

A method and apparatus for gel electrophoresis which employs periodic inversion of the electric field essentially in one dimension, denoted as field-inversion gel electrophoresis (FIGE), results in net migration by using a longer time or higher voltage in one direction than in the opposite direction. FIGE permits separation of DNA or protein mixtures in size ranges not accessible to ordinary electrophoresis.

11 Claims, 4 Drawing Sheets

OTHER PUBLICATIONS

Smith et al., *Nature* 319:701–702 (1986).
Carle et al., *Nucleic Acids Res.* 12:5647–5664 (1984).
Carle et al., *Proc. Natl. Acad. Sci.* USA 82:3756–3760 (1985).
Van der Ploeg et al., *Cell* 37:77–84 (1984).
Van der Ploeg et al., *Cell* 39:213–221 (1984).
Van der Ploeg et al., *Science* 229:658–661 (1985).
Abadi *Clin. Chem.* 15(1):35–41 (1969).
Carle et al., *Science* 232:65–67 (1986).
Delator et al., *Rev. Sci. Instrum.* 47(12):1531–1535 (1976).
Giannini et al., *Science* 232:762–765 (1986).
Schwalbe *Medical Electronics* "Proceedings of the Second International Conference on Medical Electronics" Iliffe & Sons Ltd., London England (1959) pp. 603–604.

FIELD-INVERSION GEL ELECTROPHORESIS

This application is a continuation of application Ser. No. 07/178,676, filed Apr. 7 1988 now abandoned, which is a continuation-in-part of Ser. No. 781,283, filed Sep. 27, 1985, now U.S. Pat. No. 4,737,251.

FIELD OF THE INVENTION

This invention relates to gel electrophoresis and more particularly to a method and apparatus for gel electrophoresis which employs periodic alteration, particularly inversion, of the electric field.

BACKGROUND ART

Electrophoresis involves the separation of mixtures by differential migration of components through a transport medium or support in an electric field. Many molecules and particles in aqueous solution acquire an electrical charge due to ionization and thus move in response to an external electric field. The charged particles may be simple ions, complex macromolecules, viruses, colloids or even living cells. The rate of their migration depends generally upon the amount of charge, the size and shape of the particle, and the properties of the solvent and support.

Electrophoresis in a gel support is an important method of separating proteins, nucleic acids and other such macromolecules in mixture. When an electric field is applied to the support at a given pH, the macromolecules migrate toward the oppositely charged electrode. When the support does not exert any influence, the higher the ratio of charge to mass, the faster the molecules migrate, and, application of current across the support results in a series of bands according to mass/charge ratio.

For molecules such as DNA, or proteins of analogous amino acid composition treated with a detergent such as SDS, the mass/charge ratio is often virtually identical for all these components of a mixture, since the DNA or protein molecules acquire a fairly uniform charge per repeating subunit which is roughly the same. When electrophoresed on a support having a pore size smaller than the molecules' cross section, the migration rate depends inversely on size. The mixture of macromolecules is thereby eventually separated into a series of distinct bands dependent mostly on their relative size.

The electrophoresis is generally terminated when the leading band has migrated through most of the available gel. The bands can be identified by suitable means such as staining, optical scanning and the like procedures, and the macromolecules can be recovered by cutting out and solubilizing the corresponding portions of the gel. This can be done, for example, by electroelution from the gel or by chemical or physical disruption of the gel structure followed by appropriate purification techniques.

A variety of materials can be used to obtain the gels. The gels must provide a matrix wherein the pore size is smaller than the cross-sectional dimension of the molecules to be separated, or mass/charge consideration will be determinative, and little separation will be achieved when mass/charge ratios are nearly the same. Thus, in free solution, or in gels of very large pore size, all linear DNAs have the same mobility regardless of size. It is only because of the sieving effects of the gel, wherein larger DNA molecules must find more circuitous paths, thereby slowing their progress, that separation can be achieved. But for very small pore sizes, very large molecules tend hardly to move at all, and the larger the molecules desired to be separated, the larger the pore size must be. Agarose, which is a naturally occurring linear polysaccharide of galactose and 3,6-anhydrogalactose, is particularly useful as the electrophoretic support medium since it permits the separation of large molecules such as viruses, enzyme complexes, lipoproteins and nucleic acids which are sometimes outside the useful pore size with polyacrylamide gel electrophoresis. A large variety of agaroses and modified agaroses are available commercially. They are usually used in concentrations ranging from about 0.1 to about 2.5% by weight, which gives a pore size of 10–100 Å. Polyacrylamide gels are also commonly used for smaller molecules of interest as they have smaller pore sizes, of the order of 10 Å or less. A variety of support materials has been used, and the invention is not limited to any particular support medium. However, agarose and polyacrylamide are clearly the most common and best studied, and therefore preferred by most practitioners.

Notwithstanding the foregoing, the use of conventional agarose or polyacrylamide gel electrophoresis has not generally been ideally suited for separation of the largest deoxyribonucleic acid (DNA) molecules, that is, molecules which are larger than about $2 \times 10^5$ base pairs (bp) or about 200 kb. Most practical work has been confined to molecules less than about $2 \times 10^4$ bp or about 20 kb. Although typical DNA molecules employed in genetic engineering applications are within this lower size range, the DNA molecules in chromosomes are larger.

Further background information on conventional gel electrophoresis of DNA can be had by reference to a text such as Rickwood and Hames, *Gel Electrophoresis of Nucleic Acids: A Practical Approach*, IRL Press, Oxford, UK, particularly chapter 2, "Gel Electrophoresis of DNA", by Sealey and Southern.

For background information on attempts to achieve separation of very large DNA molecules by conventional gel electrophoresis, reference can be had to papers by Fangman, *Nucleic Acids Res.* 5: 653–665 (1978); and Serwer, *Biochemistry* 19, 3001–3004 (1980). Both reports relate to the use of dilute gels, since here the pore sizes will be more in keeping with the size of the molecules whose separation is desired. In the former paper, using very dilute agarose gels (which are difficult to handle) and low voltages (which require long running times), Fangman was able to achieve a mobility ratio of bacteriophage G DNA (approximately 750 kb, where 1 kb = 1 kilobase pair = 1000 base pairs) to bacteriophage T4 DNA (approximately 170 kb) of approximately 1.4. Molecules larger than bacteriophage G were not investigated. So also in the latter paper, Serwer found that the best conditions involved dilute agarose gels run at low voltages. Molecules larger than approximately 170 kb were not investigated.

Recently, a modified gel electrophoresis technique for separating large DNA molecules was disclosed by Schwartz et al., *Cold Spring Harbor Symp. Quant. Biol.* 47: 189–195 (1983); Schwartz and Cantor, *Cell* 37: 67–75 (1984); Smith and Cantor, *Nature* (1986) 319: 701–702; and Cantor and Schwartz, U.S. Pat. No. 4,473,452. According to their disclosed technique, the DNA molecules are separated by subjecting the gel medium alternately to two non-uniform electric fields having co-planar directions which are transverse to each other. The two fields alternate between respective high and low intensities out of phase with each other at a frequency related to the mass of the particles. Because the fields are transversely applied, the DNA molecules migrate in a direction that lies between the two field directions.

Although the disclosed Cantor and Schwartz technique has been applied with success to separate DNA molecules present in the chromosomes of lower organisms such as yeast and protozoans, the bands are somewhat distorted and nonparallel, presumably because there is asserted to be an advantage, in their approach, of using non-uniform fields. It is thus difficult to make lane-to-lane comparisons between samples as is obtained in conventional gel electrophoresis. Moreover, the transverse-field gel electrophoresis technique requires complex electrode geometries. Although the theoretical minimum is three, no devices have been described that contain fewer than four, and it is common for devices to feature whole arrays of electrodes. Furthermore, the precise positioning of the electrodes has dramatic effects on the results obtained. Consequently, transverse-field-alternation gel electrophoresis does not provide for convenient gel electrophoresis practice.

Implementation of the transverse-field technique (also defined as orthogonal-field-alternation gel electrophoresis, or OFAGE) and applications to the chromosomal DNA molecules from yeast are described by Carle and Olson, *Nucleic Acids Res.* 12: 5647-5664 (1984). A description of the complete analysis of the set of chromosomal DNA molecules from yeast using the transverse-field technique is further reported by Carle and Olson. *Proc Natl Acad Sci (USA)* 82: 3756-3760 (1985).

Other background information on the application of the transverse-field technique of gel electrophoresis to chromosomal DNA molecules is provided by Van der Ploeg et al., *Cell* 37: 77-84 (1984); Van der Ploeg et al., *Cell* 39: 213-221 (1984); and Van der Ploeg et al., *Science* 229: 658-661 (1985).

DISCLOSURE OF THE INVENTION

In accordance with the present invention, an improved system for gel electrophoresis has been devised which is suitable for the separation of a wide range of molecules including very large DNA (for example, chromosomal DNA) and protein molecules, and which provides parallel bands of the separated compounds. The method and apparatus of this invention employs periodic alteration, especially inversion, of an electric field in only one dimension. For convenience, this system can be described as field-inversion gel electrophoresis or FIGE.

According to the invention, net migration of at least one component of the mixture to be separated or a sample to be analyzed is obtained by a systematic out-of-phase variation in the intensities of two fields in a colinear dimension imposed on an electrophoresis gel support containing the mixture of materials to be separated or sample to be analyzed. Preferably the fields are repetitively applied alternately in opposite directions. Thus, in its simplest and preferred form, this out of phase variation can be thought of as a simple reversal of the direction of the field wherein the net migration of molecules in the sample is achieved by using a longer time or a higher voltage in one direction than in the other direction. However, the invention is not limited to this particular protocol, but includes modulation of the field in a unidirectional sense.

For the preferred case where field inversion is employed, net migration in a given direction can be achieved, for example, by partitioning each switching cycle unequally in time between so-called "forward" and "reverse" directions or by imposing a higher voltage in the forward direction than in the reverse direction, or some combination of these. Resolution can be optimized in a given size range by selecting an appropriate repetitive switching regime. Conversely, a broad size range can be explored by employing switching-interval gradients, in which the period or voltage pattern of the internal structure of the switching cycle is varied during an electrophoresis run.

The successful results achieved with the field-inversion gel electrophoresis system of this invention were surprising and unexpected in view of prior experience with electrophoresis. They were also not predictable from existing molecular theories of electrophoresis. Although the inventors are not bound by any particular theory, the phenomenology of the system is believed to be based on the adoption of directional conformations by macromolecules during the electrophoresis as will be seen from specific examples and explanation hereinafter.

For many types of macromolecular mixtures, the present invention provides substantial improvements over the transverse-field technique in resolution, experimental convenience, and practical-sample capacity.

MODES OF CARRYING OUT THE INVENTION

A. General Description

Figure 1:
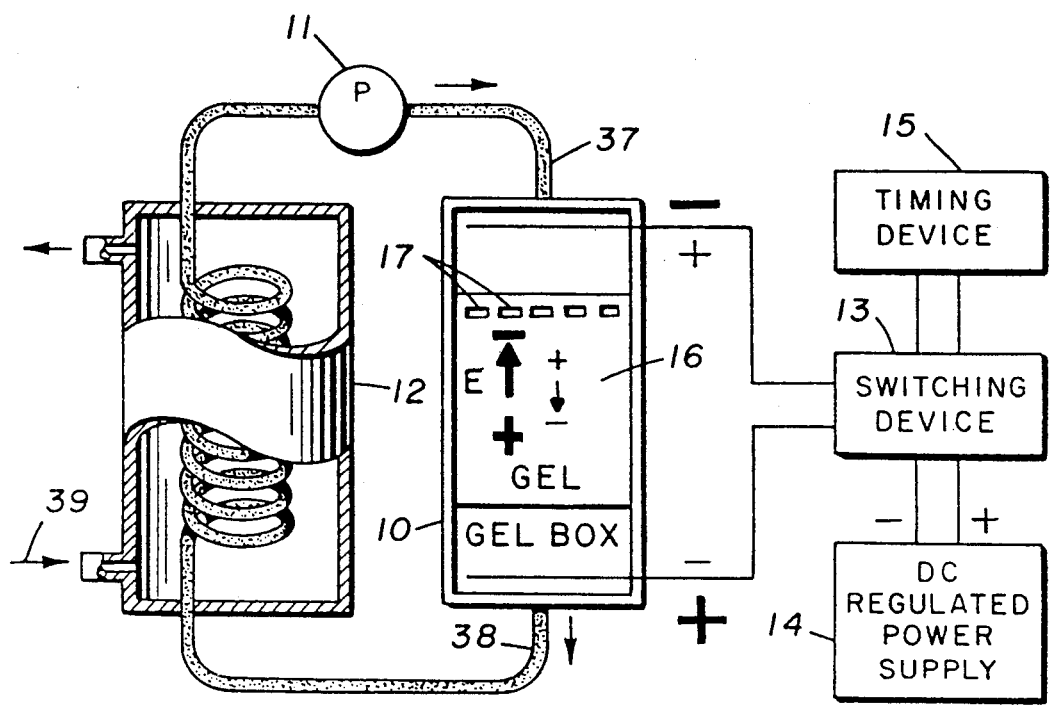
FIG. 1 is a schematic diagram of the field-inversion gel electrophoresis system in one embodiment of the invention.

While the specification concludes with claims particularly pointing out and distinctly claiming the subject matter regarded as forming the present invention, it is believed that the invention will be better understood from the following detailed description of preferred embodiments and explanation of a theoretical model.

Although the inventors are not bound by any particular theory, the results obtained in the field-inversion gel electrophoresis method can be explained by assuming the adoption of directional conformations by macromolecules during the electrophoresis. Under steady-state electrophoresis, a molecule can be regarded schematically as an arrow, in which the leading portion of the molecule is in a different conformation than the trailing portion. The model assumes that a molecule has a much higher mobility when the arrow is aligned with the field than when it is oppositely aligned, or perhaps even in some intermediate conformation. It is also assumed that a size-dependent time interval is required for a molecule to invert the directionality of its conformation. When the field-inversion cycle has a period that is closely matched to the interval required for a particular sized molecule's conformational inversion, that molecule has very low mobility since it spends little or no time in a conformation that is appropriately aligned with the field. This "resonance" phenomenon explains the minimum-mobility effect observed in the application of this method and further described in Example 1, below. The largest molecules are completely unable to keep up with the changing fields and adopt a steady-state conformation that has higher mobility than a molecule that is at or near resonance, but still much lower than the mobility of molecules than can re-orient rapidly compared to the field-inversion period.

Thus, it is clear that various portions of the molecular weight scale can be expanded or contracted by using proper choices for the switching regime. A constant switching regime in resonance with a particular molecular weight will result in expansion of the separation distances of molecules whose molecular weights fall to either side of it. Also, in general, higher frequencies have "resonances" with smaller molecules; lower frequencies with larger ones. While the precise program which is most effective for a particular mixture depends on a number of factors and cannot be predicted precisely, a general estimate can be made using the foregoing generalization.

In addition, a larger spectrum of molecular weights can be conveniently separated by employing ramped scales. In their simplest form, such scales progressively increase or decrease the intervals in each direction during the course of the electrophoresis so that the ratio of the intervals remains the same, although their absolute length continuously rises or falls. In another variant, one interval, e.g., the "backward" interval is held constant while the opposite interval consistently increases or decreases. This sort of orderly pattern is, of course, not necessary, and a constant ratio by no means needs to be maintained in order to effect a satisfactory separation in a particular case. However, such straightforward ramping regimes provide a convenient starting point, and there is no necessarily advantageous effect to be had in making the program more complicated.

A number of the variations on the switching programs are illustrated in the examples below. These include maintaining the same time interval for forward and reverse directions but varying the voltage; maintaining the same voltage levels but altering the time spent in each direction, and the just described ramping regimes. Additional programs, so long as they require multiple application of fields in opposite directions along a unit dimensional gel are included within the scope of the invention.

Also included in the invention are pulsed field variations, again unidirectional, in which the net voltage is not necessarily reversed. Such programs take advantage of high voltage spurts alternating with lower voltage application in the same direction across the gel. The foregoing model also is helpful in explaining this variant. The ability of a modulated field to effect separations in a manner similar to that obtained by field-inversion also relies on differential changes in conformation. For long, narrow molecules such as DNA chains or denatured proteins, the migrating materials may behave more or less like "spaghetti". If a relatively low voltage is imposed across the support, the spaghetti has time to unravel itself and migrate cleanly through the pores in the direction corresponding to the electric field interacting with its charge. On the other hand if the voltage is suddenly spiked the charged portions across the entire length of the molecule are suddenly thrust against the barriers in the matrix preventing successful forward motion. Thus, when extremely steep and high magnitude voltage fields are applied in the "forward" direction, alternating with low voltages, migration rate also depends on the rate of reconformation and, in field modulation, the "reverse" direction can, in a sense, be mimicked by the forward voltage.

The power of the field-inversion invention lies in the addition of a new variable to a standard electrophoresis run, which profoundly alters the electrophoretic behavior of many types of molecules, while retaining the powerful flexibility that characterizes conventional electrophoresis (i.e. many simple apparatus designs, types of electrophoretic media, etc.). This new variable is the field-inversion switching regime. The switching regime can be simple (e.g., a constant cycle with 10 sec "forward" and 5 sec "backward") or complex (e.g., a systematically varying cycle during a run), depending on the desired result. A dramatic illustration of the power of the switching regime to alter electrophoretic mobilities is provided by the minimum-mobility phenomenon; under some conditions a strong direct (rather than the usual inverse) correlation between size and mobility can be created. This "limb" of the size-mobility curve may be more effective than the conventional limb for some separations. When it is undesirable, because it leads to a region in the gel in which molecules of two greatly different sizes can unexpectedly have the same mobility, it can be minimized or eliminated by the use of switching-interval gradients, or appropriately chosen constant switching cycles.

As is the case with conventional electrophoresis, in field-inversion gel electrophoresis, large numbers of samples that have been loaded onto adjacent lanes of a single gel will migrate in parallel with one another, experiencing closely comparable electrophoretic conditions. The ability to make reliable, lane-to-lane comparisons between many samples on the same gel is one of the strongest features of conventional electrophoresis. It may or may not be possible to achieve simple, parallel migration patterns by the transverse-field technique, but most reported applications have failed to achieve this goal. The importance of this point arises because many electrophoretic procedures depend on comparisons between the mobilities of molecules migrating in different lanes, and experimental flexibility is at a maximum when good comparisons can be made between samples that are several lanes apart. One example of an application of this type is the estimation of molecular sizes by comparing the mobility of a molecule of unknown size in one lane with that of a molecule of known size in a different lane. Another example, which does not require absolute size calibration, concerns efforts to determine whether or not molecules in different samples are potentially identical or demonstrably non-identical by determining whether or not they have the same or different mobilities.

Because of its capability of enhancing standard electrophoretic practise while imposing minimal demands on the design of the core components of an electrophoresis apparatus or the distribution of samples across a gel, field-inversion electrophoresis has a wide spectrum of potential applications. Its capability of enhancing the ability to resolve large DNA molecules has been demonstrated above over a size range from 15 kb to >700 kb, where the uncertainty in the upper limit of the demonstrated range of application arises because of a lack of well characterized test molecules >700 kb in size. It is highly likely that the applicable size range can be expanded both to smaller and larger sizes by changes in such easily varied test conditions as the temperature, the switching regime, the composition of the electrophoretic medium, the forward and/or backward voltage, the composition of the running buffer, and the duration of the run. All these variables can be optimized for the best results for specific applications of the electrophoresis in which more sensitive effects could be obtained with the field-inversion method than with conventional electrophoresis.

In all of the foregoing, good temperature control is preferred because it is likely that the activation energy of the conformational changes described above is high enough to impart a temperature dependence to the mobilities of molecules in field-inversion gel electrophoresis that is greater than that observed in conventional electrophoresis.

B. Subject Substances

The applications of the field-inversion technique are not limited to DNA. The qualitative electrophoretic behavior of other charged macromolecules such as RNA, protein, nucleoprotein particles, and protein-detergent complexes is generally similar to that of DNA, and the field-inversion method is expected to increase the size range over which these molecules can be separated and allow enhanced resolution in particular size ranges that are targeted by an appropriate choice of the switching regime.

The examples herein illustrate the technique in separating DNA molecules because of the intrinsic interest in obtaining such separations in analysis. However, it should be noted that the technique is equally applicable to other molecules capable of assuming a reasonably evenly distributed charge. Among such molecules of considerable importance are the proteins which when denatured in anionic or cationic detergents assume more or less uniform charge across the primary structure. Using the method of the invention, not only are proteins of conventional molecular weights of the order of 20–50 kd susceptible to separation, but also higher molecular weight proteins such as factor VIII, which has a molecular weight of about 240 kd.

C. Apparatus for FIGE

Field-inversion gel electrophoresis can be carried out in a variety of much simpler apparati than required for transverse-field electrophoresis. Indeed, with the exception of the external timing and switching devices and, in some instances, improved temperature control, the field-inversion system can be carried out in an ordinary electrophoresis apparatus. This lack of a requirement for a gel box and electrode system of specialized design is of great importance since a large variety of electrophoresis apparati have been designed to maximize the convenience of sample handling and gel preparation, the speed of separations, the amount of sample required, the ease of visualizing the separated molecules, and other experimental variables. In all these cases, it would be useful to be able to separate larger molecules and to increase the resolution in targeted portions of the accessible size range. The field-inversion methods offers a general solution to this problem that depends on external accessories rather than the core electrode/running buffer/gel unit. In contrast, the transverse-field-alternation gel electrophoresis of the art requires complex electrode geometries, and the precise positioning of the electrodes has dramatic effects on the results obtained. Consequently, transverse-field-alternation gel electrophoresis, unlike the field-inversion technique, does not offer a convenient way of building on and greatly extending the utility of standard electrophoretic practice.

Figure 2:
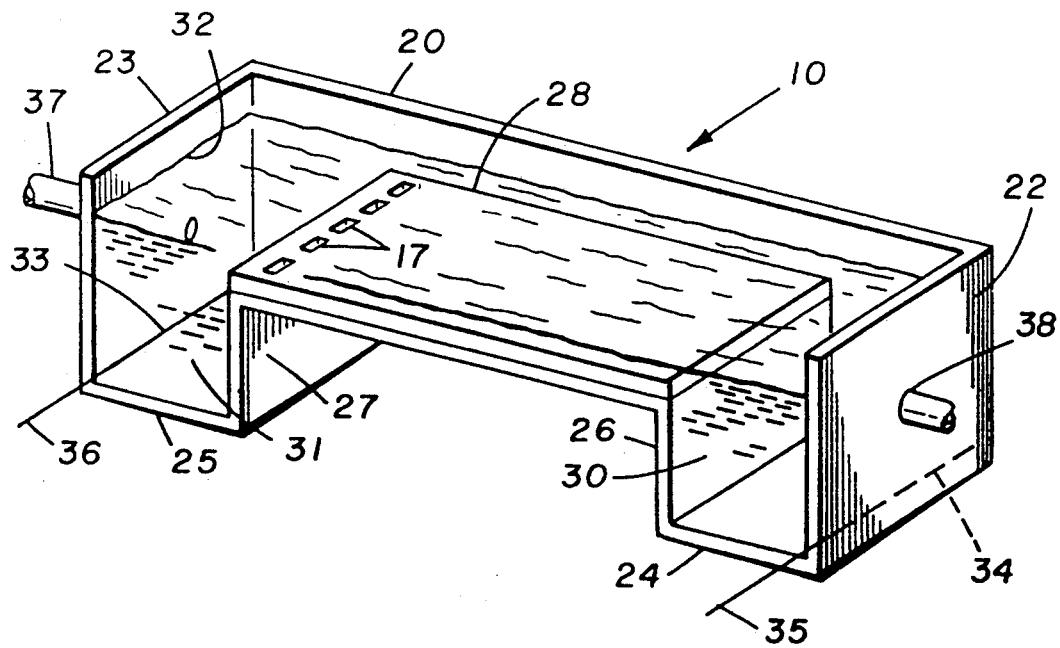
FIG. 2 is a perspective, partly in cut-away view, of a gel box in one embodiment of the invention.
Figure 3:
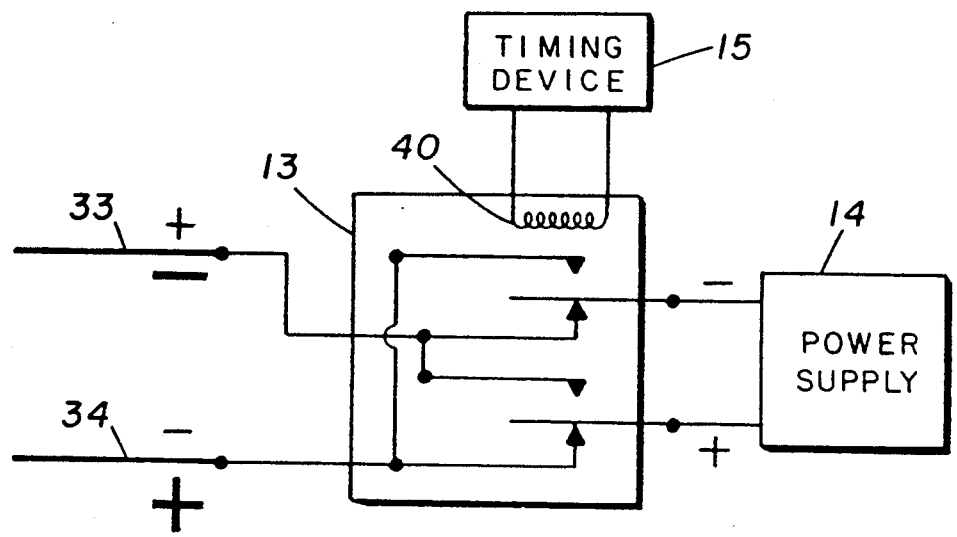
FIG. 3 is a wiring diagram of a switching component to provide switching intervals in the field inversion gel electrophoresis of FIG. 1.

Referring now to the drawings, a laboratory embodiment of the field-inversion gel electrophoresis system of this invention is illustrated in FIGS. 1 to 3. With particular reference to the schematic diagram in FIG. 1, the field-inversion gel electrophoresis system is illustrated by a series of interconnected components comprising an electrophoresis chamber or gel box 10, a pump 11, a heat exchanger 12, a switching means 13, a DC regulated power supply 14 and a timing device 15.

In the schematic diagram of FIG. 1, a top view of the gel box is illustrated in which the gel layer or slab 16 and a series of sample wells 17 cast into the gel at one end of the gel layer are shown. The longer arrow and larger polarity signs (+ and −) indicate the predominate condition. That is, in variations in which net migration is achieved by applying the same voltage in both directions, the predominant condition is one that is applied for the larger fraction of each switching cycle; in variations in which different voltages are applied for the same interval, the predominant condition would be the higher voltage. The usual convention of arrows pointing from + to − signifying the electrical-field (E) is employed in the figures. Because most macromolecules, including DNA, are negatively charged under electrophoretic conditions, the direction of migration is in the opposite direction of the large arrows.

The internal structure of gel box 10 is shown in greater detail in FIG. 2. The gel box comprises a generally rectangular sided chamber having sidewall 20, endwalls 22 and 23, and base portions 24 and 25. A front sidewall which would lie opposite the rear sidewall 20 is not shown in the cut-away view of FIG. 2. The gel box is further provided with a raised platform or tray 28 in a plane below the top of the gel box and supported at opposite ends by partition walls 26 and 27. This platform serves as a support for the gel layer 16. The side-, end-, and partition-walls at each end of the gel box also form buffer chambers in an amount sufficient to cover the gel layer as shown by the buffer level 32.

Electrodes 33 and 34 made of electrochemically inert material and having suitable electrical conducting properties, for example platinum, are provided for retention within the buffer chambers 30 and 31 respectively. They are preferably positioned along the endwalls at the bottom of the buffer chambers with electrical leads 35 and 36 for connection to the switching means 13.

Tubing 37 and 38 with openings into buffer chambers 30 and 31, respectively, are provided for re-circulation of buffer from the gel box through a heat exchanger 12 by pump 11. The heat exchanger serves to dissipate heat generated within the gel box during electrophoresis. The cooling fluid source 39 for the heat exchanger can be provided by a conventional re-circulating, refrigerated water bath (not shown).

The switching means 13 is critical to the provision of the periodic field-inversion of the gel electrophoresis. This system in essence can comprise a power relay device. FIG. 3 is a circuit schematic that indicates the manner in which the power relay can be wired. The relay is shown in its relaxed configuration. When the timing device 15 supplies voltage to the relay's coil 40, the relay switches to its activated configuration, thereby inverting the polarity of the electrodes.

With a switching system as described above, the timing device 15 essentially controls when line voltage is or is not supplied to the coil of the power relay.

The power supply can be any suitable source of direct current.

In the embodiment illustrated by FIGS. 1 to 3, the apparatus is in a configuration that allows field-inversion electrophoresis to be carried out at a constant applied voltage with a larger portion of the switching cycle devoted to forward migration than to reverse migration. In variations in which a higher voltage is applied in one direction than the other, more complex electrical circuitry is required. For example, two power supplies can be employed, wired through separate power relays to independently programmable output circuits of the timing device.

Various components which can be used in the gel electrophoresis apparatus of this invention are commercially available. For example, gel electrophoresis chambers for use in the horizontal mode can be obtained from various sources such as Bethesda Research Laboratories (Gaithersburg, Md.) Model 144 Horizontal Gel System; Bio-Rad (Richmond, Calif.) Model 1405 and 1415 Electrophoresis Cells; Pharmacia (Uppsala, Sweden) FBE 3000 and GNA-200 Flatbed Cells; and the LKB (Bromma, Sweden) 2117 Multiphore II Electrophoresis Unit. Such devices can be adapted for use in the invention by appropriate combination with the other components specified herein to provide the periodic field-inversion.

Alternatively, the simplified gel box as shown in FIG. 2 can be readily fabricated from rigid materials such as, for example, acrylic plastic. Thus, a conventional laboratory scale gel box can be constructed from 0.25 inch thick clear acrylic plastic with inside dimensions 8.5×14 inches as viewed from the top. The gel platform can be 8.5×8.5 inches set in a plane 1.5 inches below the top of the gel box. Buffer chambers at the two ends can extend to a depth of 3.4 inches from the top of the gel box. Electrodes 8.5 inches log, 100% platinum (26 gauge), can be set directly against the intersection of the end walls and the bottom of the buffer chambers.

For a gel box of the foregoing size, buffer can be suitably re-circulated at a rate of about 250 ml/minute using, for example, a Cole Parmer (Chicago, Ill.) Masterflex T-7553-00 drive with a T-7018-21 head equipped with silicone tubing with 5/16 inch inner diameter.

It will be appreciated, however, that the invention is not limited to the foregoing measurements or to the specific illustrative equipment disclosed herein which are provided for exemplification of the invention and not limitation. Other representative equipment which is commercially available can also be used to provide the heat exchanger, switching means, power supply and timing device. Thus the heat exchanger can be fabricated from polyethylene tubing as described by Carle and Olson, *Nucleic Acids Res.* 12: 5647–5664, at 5651 (1984). The cooling fluid source and the ultimate heat sink, can be a Neslab Instruments (Portsmouth, N.H.) Model RTE-98 re-circulating, refrigerated water bath.

The power relay can be, for example, a Deltrol Controls (Milwaukee, Wis.), Series 900 DPDT No. 20241-83. For higher voltages or faster switching intervals, various other switching devices are available such as vacuum relays, solid-state relays, and the like.

Illustrative power supplies are the Heathkit (Benton Harbor, Mich.) 18-2717 Regulated High Voltage Power Supply and the Hewlett Packard (Berkeley Heights, N.J.) SCR-1P Model 6448B DC Power Supply.

With a switching system as illustrated above, the timing device merely needs to control when line voltage is or is not supplied to the coil of the power relay. For repetitions of a switching cycle that does not vary during a run, a laboratory timer such as a Lindburg Enterprises (San Diego, Calif.) Chrontrol Model CT-4 can be used. For runs during which the switching cycle is varied, an International Business Machines (Boca Raton, Fla.) Personal Computer can be programmed to produce the desired, temporarily varying pattern of standard TTL signals at the output pins of the printer adapter; and these signals can be used to control the line voltage to the coil of the relay in the switching system by way of a Sigma (Braintree, Mass.) Series 226 Model 226R1-5A1 Solid-State Relay.

D. Examples

The following examples will further illustrate the invention although it will be understood that the invention is not limited to these specific examples or the specific details recited therein.

EXAMPLE 1

This example illustrates the separation of DNA's in the size range 15–300 kb using a constant switching cycle in the apparatus illustrated by FIGS. 1 to 3. The cycle used 300 volts for 3 seconds in a forward direction followed by 300 volts for 1 second in the opposite direction. The results are shown in FIG. 4.

Samples included bacteriophage λ DNA cleaved with the restriction endonuclease XhoI, intact bacteriophage λ DNA, DNA from bacteriophage T5 and T4, and total DNA from the yeast (*Saccharomyces cerevisiae*) strain AB972. The λ DNA and the XhoI digest of λ DNA were handled by a standard sample preparation and gel loading procedures as described by Sealey and Southern, *supra*. The T4 and T5 DNA's were prepared as described by Carle and Olson, *Nucleic Acids Res.* 12: 5647, 5664 (1984) (hereinafter ref. 1), and the yeast DNA was prepared as described by Carle and Olson, *Proc Natl Acad Sci (U.S.A.)* 82: 3756–3760 (1985) (hereinafter ref. 2).

The running buffer was 00.5×TBE, as described in Carle and Olson, ref. 1 (1×TBE=90 mM Tris Base, 90 mM boric acid, 2.5 mM $Na_2H_2EDTA$, unadjusted pH~8.2). The switching regime involved 3 sec in the forward direction followed by 1 sec in the backward direction, with this cycle repeated for 12 hrs. A constant voltage of 300 V was employed under which conditions the apparatus drew a current of approximately 100 mA. The gel composition was 1% (wt/vol) agarose and the temperature of the re-circulating buffer was approximately 13°.

Figure 4:
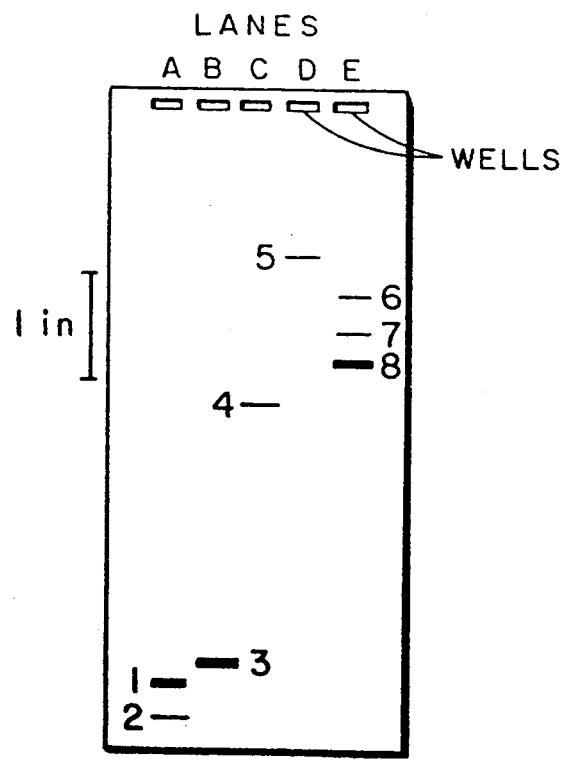
FIG. 4 represents the electrophoretic pattern of bands obtained using a constant voltage switching cycle.

FIG. 4 shows the pattern of bands obtained in this example using a 5-lane region of the gel. A scale representing one inch of separation is shown at the left side of FIG. 4. The horizontal lines numbered 1-8 are the bands, which were visualized by conventional ethidium-bromide staining of the gel as described by Seale and Southern, *supra*, with the detailed staining and visualization conditions as described by Carle and Olson, refs. 1 and 2. The samples loaded in the 5 lanes were as follows:

Lane A: Bacteriophage λ DNA, cleaved with the restriction enzyme XhoI; Band 1(33.5 kb), Band 2 (15.0 kb),
Lane B: Bacteriophage λ DNA; Band 3 (48.5 kb)
Lane C: Bacteriophage T5 DNA; Band 4 (approx. 125 kb)
Lane D: Bacteriophage T4 DNA; Band 5 (approx. 170 kb)
Lane E: Yeast (*Saccharomyces cerevisiae*, strain AB972) chromosomal DNA; Band 6 (chromosome I, est. 260 kb); Band 7 (chromosome VI, est. 290 kb); Band 8 (approx. 14 remaining chromosomes est. 300 kb to >1000 kb)

As shown in FIG. 4, the above conditions provide particularly good separation between λ and T5 DNA. Surprisingly, T4 DNA has a lower mobility under these conditions than *either* the smaller T5 molecule or the larger yeast thromosomes. This phenomenon of a minimum mobility in a particular size range that can be selected by varying the switching regime, is typical of field-inversion gel electrophoresis. The larger yeast chromosomes all have approximately the same mobility under these conditions, producing a single broad band.

EXAMPLE 2

Figures 5, 6:
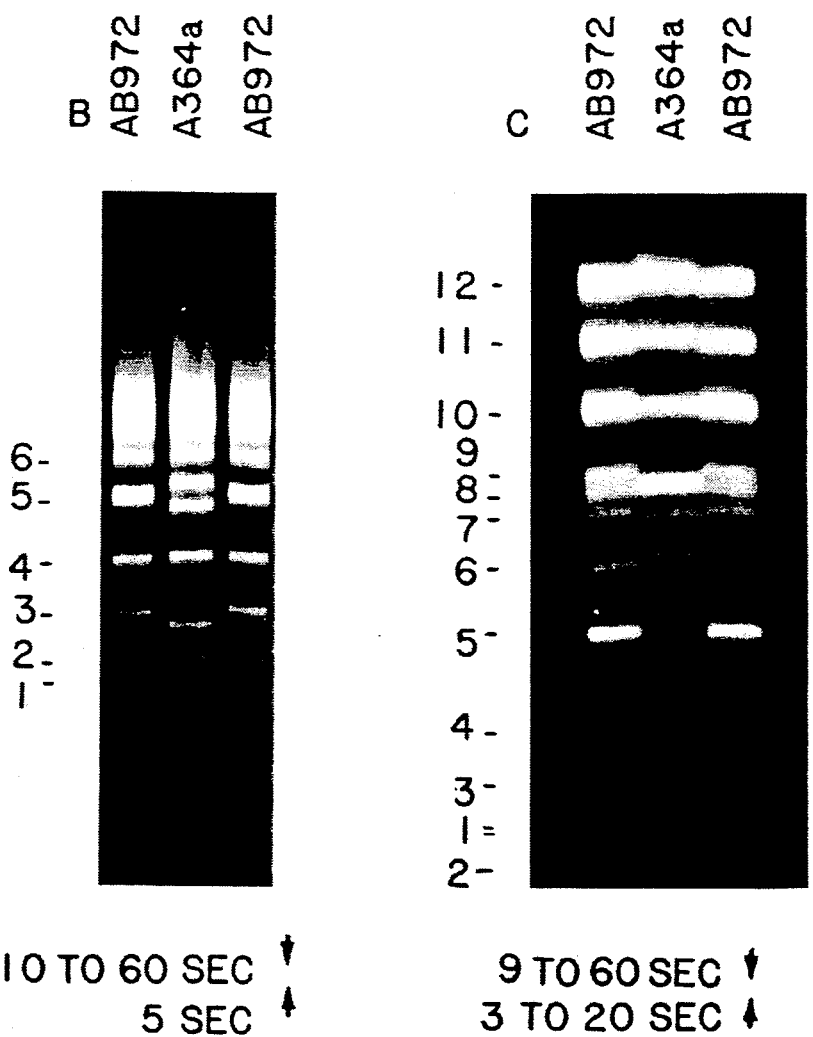
FIG. 5 represents the electrophoretic pattern of bands obtained using a constant voltage and a linearly varying cycle with constant ratio between forward and backward intervals.
FIG. 6 represents the electrophoretic pattern of bands obtained using constant voltage but varying time intervals of increasing ratio.
Figure 7:
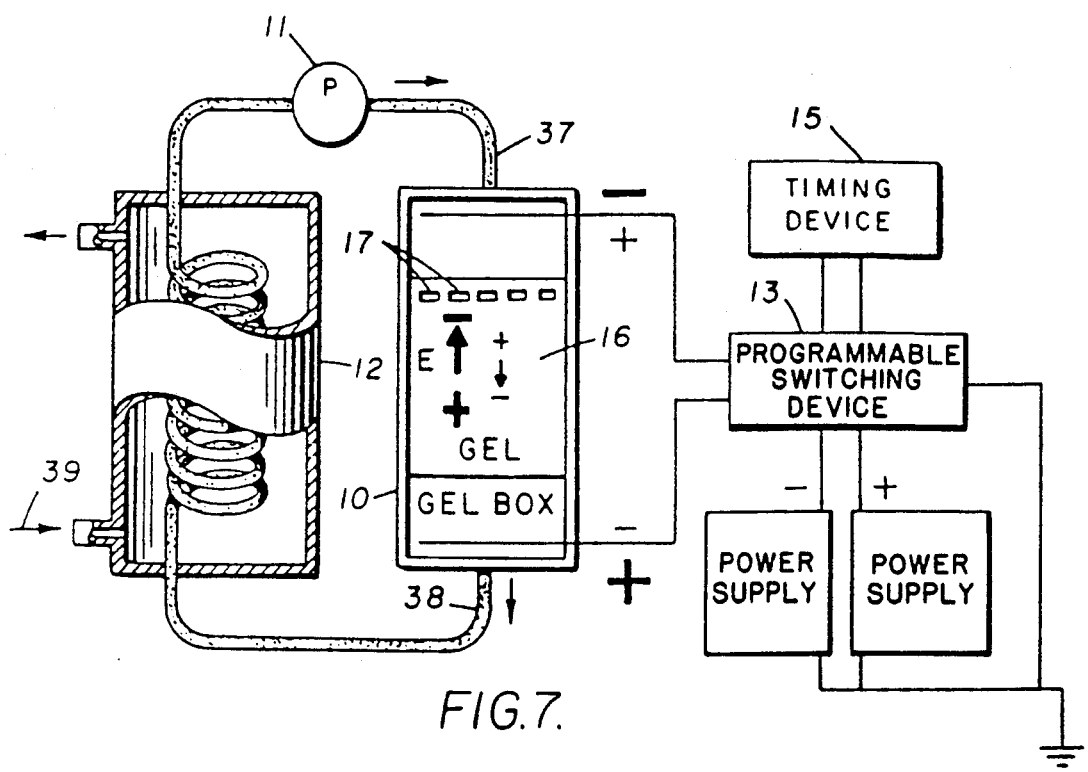
FIG. 7 is a schematic diagram of the field-inversion gel electrophoresis system in a second embodiment of the invention. In particular, a switching device which is programmable and two variable power supplies are shown.
Figure 8:
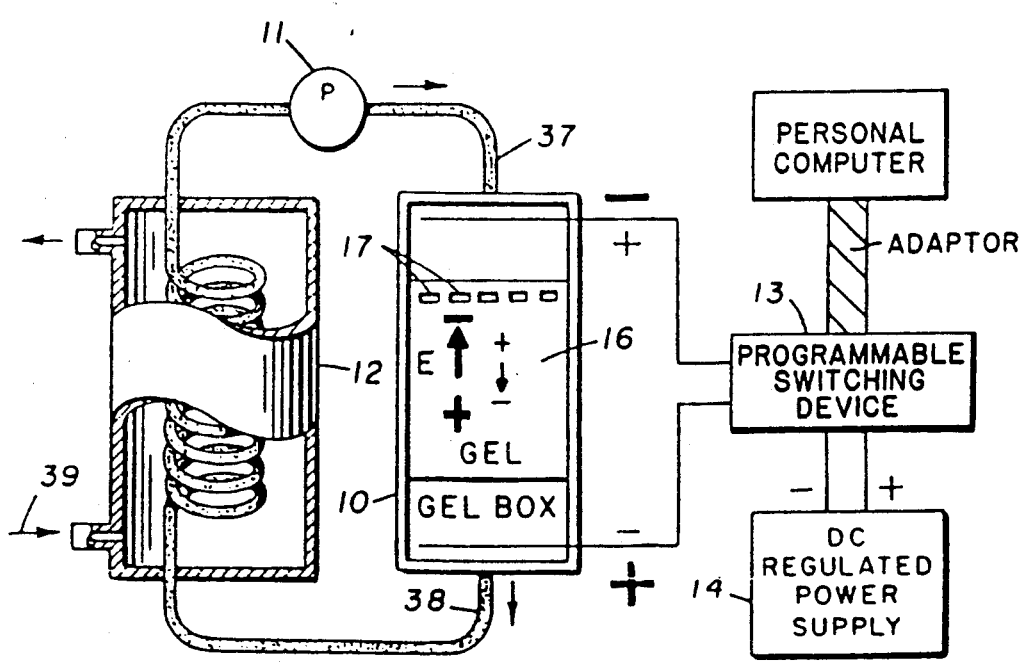
FIG. 8 is a schematic diagram of the field-inversion gel electrophoresis system in a second embodiment of the invention. In particular, a switching device which is programmable and a personal computer which is attached by an adaptor are shown.

This example illustrates the separation of DNA's in a size range estimated to be 260 kb to >700 kb using a swtiching-interval gradient with a constant ratio between the forward interval and the backward interval. The results are shown in FIG. 5.

The samples were yeast DNA from strains AB972 (Example 1 above) and A364a, prepared as described in Carle and Olson, ref. 2. The experimental conditions were identical to those in Example 1 except that the voltage was 260 volts rather than 300 volts, and the switching regime involved a linearly varying cycle starting at t=0 hr with 9 sec forward, 3 sec backward and ending at t=20 hr (the end of the run) with 60 sec forward and 20 sec backward.

The pattern was qualitatively similar to that obtained by transverse-field gel electrophoresis described in Carle and Olson, ref. 2. Good separation was obtained of bands 1-9, using the numbering system of the reference, and also shown in FIG. 5. For example, the two components of band 5 (bands 5A and 5B, Carle and Olson, ref. 2), were separated in the A364a pattern by approx. 0.3 in. Three broad, intense bands with lower mobility than band 9 were also present and well separated from one another as shown. The sizes of the molecules in bands 1-6 have been estimated in Carle and Olson, ref. 1, to span the range 260-700 kb; the molecules in bands 7-9 are thought to be progressively larger than band 6, but size estimates are unavailable.

EXAMPLE 3

This example illustrates the separation of DNA's in a size range estimated to be 260 kb to 700 kb using a linear gradient of forward intervals with a constant backward interval. The results are shown in FIG. 6.

The samples and experimental conditions were similar to those in Example 2 with the exception that the switching regime involved a linearly varying forward interval starting at t=0 hr with 10 sec forward and ending at t=12 hr with a forward interval of 60 sec, while the backward interval was held constant at 5 sec. Excellent separation was obtained in the region of bands 1-6, using, again, the numbering system described in Carle and Olson, ref. 2, as shown in FIG. 6.

Once again, the pattern was qualitatively similar to that obtained by transverse-field gel electrophoresis. In comparison to Example 2, better resolution was obtained in the region of bands 1-4, while bands 5 and 6 were more compressed, and the remaining DNA migrated behind band 6 in a broad band with indistinct components. For example, in the AB972 pattern, the overall separation from band 1 to band 4 was approximately 1 inch, with a clear separation of all bands within this interval. The sizes of the molecules in these bands have been estimated in Carle and Olson, ref. 1, to be 260 kb (band 1), 290 kb (band 2), 370 kb (band 3) and 460 kb (band 4).

EXAMPLE 4

This example illustrates the separation of DNA's in the size range 15-300 kb, with particularly effective results in the region from 50-125 kb. Unlike the previous examples, the time interval for the forward and reverse portions of the switching cycle were identical, while the applied voltages differed. The samples were the same as those specified in Example 1. The voltage in the forward direction of 350 volts, while that in the reverse direction of 250 volts. The switching cycle involved 2 seconds for both the forward and reverse intervals. The overall running time was 16 hours. Other conditions for the test were as described for Example 1.

In wiring the apparatus for this test, separate power supplies were employed to apply the forward and reverse voltages. Each power supply was connected to the electrodes through a separate power relay in such a way that the power supply was connected to the electrodes with the appropriate polarity when its relay was activated. The coils of the two relays were connected to independently programmable output circuits of the timing device, which was programmed to incorporate a 0.1 second delay between deactivating one relay and activating the other in order to eliminate the possibility that both relays might be activated simultaneously for a brief interval during the switching event.

The results were similar to those obtained in Example 1 with the best resolution occurring in the region between λ (48.5 kb) and T5 (125 kb) DNA. T4 (170 kb) DNA and the smallest yeast chromosome (260 kb) had negligible mobility, while the largest yeast chromosomes (2300 kb) all had mobilities similar to that of T5 DNA.

Various other examples of the invention will be apparent to the person skilled in the art after reading the disclosure herein.

We claim:

1. An apparatus for controlling the differential net migration of charged macromolecular substances through a gel support in a single dimension, the extent of said migration being dependent on molecular size, said apparatus comprising:

a power supply for providing an electric field along said single dimension of said gel support, timing means operably linked to programmed circuitry controlling the timing means so as to permit variation of the time intervals during said migration to provide repeated inversion of the electric field, wherein the repeated inversion comprises cycles each consisting essentially of a first voltage in one direction of polarity for a first time interval, and a second voltage in the opposite direction of polarity for a second time interval, in such manner that the migration effected by the total first voltages and first time intervals over all cycles does not equal the migration effected by the second voltages and second time intervals over all cycles, and whereby said repeated inversion of fields and periodic reversals thereof being selected to control the distance of migration of said macromolecular substances so that the distance of migration of said substances with respect to each other is determined by the selection of said repeated inversion of fields and periodic reversals thereof.

2. The apparatus of claim 1 wherein each first voltage is equal to each second voltage and the total of the first time intervals is different from the total of the second time intervals.

3. The apparatus of claim 1 wherein each first time interval is equal to each second time interval and each first voltage is different from each second voltage.

4. The apparatus of claim 1 wherein for each successive cycle the first voltage bears the same ratio to the second voltage and the first time interval is equal to the second time interval, and wherein the magnitudes of said first and second voltages are monotonically greater or less in each successive cycle.

5. The apparatus of claim 1 wherein for each successive cycle, the first time interval bears the same ratio to the second time interval, and the first voltage is equal to the second voltage, and wherein the first and second time intervals are monotonically greater or less in each successive cycle.

6. The apparatus of claim 1 wherein the repeated inversion comprises a protocol consisting of equal voltages alternating in opposite directions of polarity wherein said fields have a longer total time duration in the direction of net migration.

7. The apparatus of claim 1 wherein the repeated inversion comprises a protocol consisting of equal time periods of fields of a voltage in one direction of polarity higher than the voltage in opposite direction of polarity, wherein the net migration is in the direction compatible with the higher voltage field.

8. The apparatus of claim 1 wherein the repeated inversion comprises a protocol consisting of a repeating cycle of a first voltage in one direction of polarity for a first time interval and a second voltage in the opposite direction of polarity for a second time interval wherein the first voltage is different from the second voltage and the first time interval and second time interval are equal.

9. The apparatus of claim 1 wherein the repeated inversion comprises a protocol consisting of a repeating cycle of a first voltage in one direction of polarity for a first time interval and a second voltage in the opposite direction of polarity for a second time interval wherein the first and second voltages are equal and the first time interval is different from the second time interval.

10. The apparatus of claim 1 wherein the repeated inversion comprises a protocol consisting of a sequence of cycles wherein for each cycle a voltage is applied in one direction of the single dimension for a first time interval and is followed by application of a second voltage in the opposite direction of said single dimension for a second time interval and repetitive iterations of said cycle, wherein for each cycle of the sequence the first voltage bears the same ratio to the second voltage and the first time interval is equal to the second time interval, and wherein the magnitudes of said first and second voltages are monotonically greater or less in each successive cycle of the sequence.

11. The apparatus of claim 1 wherein the repeated inversion comprises a protocol consisting of a sequence of cycles wherein for each cycle a voltage is applied in one direction of the single dimension for a first time interval and is followed by application of a second voltage in the opposite direction of said single dimension for a second time interval and repetitive iterations of said cycle, wherein for each cycle of the sequence the firdt voltage is equal to the second voltage, the first time interval bears the same ratio to the second time interval, and said first and second time intervals are monotonically greater or less in each successive cycle of the sequence.

* * * * *